United States Patent [19]

Tanaka et al.

[11] 4,336,327

[45] Jun. 22, 1982

[54] SILVER HALIDE EMULSION CONTAINING YELLOW COUPLER

[75] Inventors: Mitsugu Tanaka; Momotoshi Tsuda, both of Minami-ashigara, Japan

[73] Assignee: Fuji Photo Film Co., Ltd., Kanagawa, Japan

[21] Appl. No.: 217,302

[22] Filed: Dec. 17, 1980

[30] Foreign Application Priority Data

Dec. 17, 1979 [JP] Japan ................. 54-163721

[51] Int. Cl.$^3$ .............................................. G03C 1/40
[52] U.S. Cl. .................................. 430/556; 430/557; 430/558
[58] Field of Search ............... 430/556, 557, 558, 338, 430/339, 475, 476

[56] References Cited

U.S. PATENT DOCUMENTS 4,012,259 3/1977 Okumura et al. .................. 430/557
4,238,564 12/1980 Fryberg .............................. 430/556
4,248,961 3/1981 Hagen et al. ........................ 430/556

Primary Examiner—J. Travis Brown
Attorney, Agent, or Firm—Sughrue, Mion, Zinn, Macpeak & Seas

[57] ABSTRACT

A silver halide color photographic light-sensitive material containing a yellow color coupler represented by the following general formula (I):

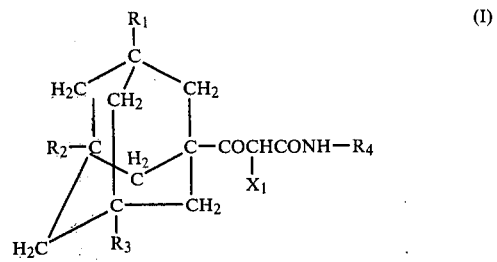

wherein $R_1$, $R_2$ and $R_3$, which may be the same or different, each represents a hydrogen atom, a methyl group or a halogen atom; $R_4$ represents an aryl group which may be substituted; and $X_1$ represents a hydrogen atom or a group capable of coupling off.

The color photographic light-sensitive material provides a yellow color image having exceptional fastness to light.

12 Claims, No Drawings

SILVER HALIDE EMULSION CONTAINING YELLOW COUPLER

BACKGROUND OF THE INVENTION

1. Field of the Invention

This invention relates to yellow couplers which provide, upon coupling reaction with the oxidation product of a primary amine developing agent, a dye having excellent light fastness (hereinafter merely "fastness" for brevity).

2. Development of the Invention

In the field of color light-sensitive materials, it has long been desired to maintain images in their initial state following development state for extended periods of time without change. Enhancing the light fastness of a dye formed from a coupler is the most basic means to reach this object. However, unlike cyan couplers and magenta couplers, yellow couplers do not provide a dye having improved light fastness even when they are used together with an anti-fading agents, rather, they provide dyes of deteriorated light fastness. Therefore, for yellow couplers it has been particularly desired to enhance the light fastness of a dye formed from such a coupler.

Heretofore, as yellow couplers which provide dyes having good fastness to light those having a pivaloyl group or a derivative thereof as disclosed in U.S. Pat. No. 3,265,506 have been suggested. However, these couplers have insufficient fastness and thus it has been desired to synthesize couplers which provide dyes having further improved fastness to light.

SUMMARY OF THE INVENTION

An object of the present invention is to provide yellow couplers which provide, upon coupling reaction, dyes having good light fastness wherein other photographic properties of the couplers are not sacrificed in order to attain this object.

This and other objects of the present invention which will be readily apparent from the following disclosure are reached by means of novel yellow color couplers represented by general formula (I):

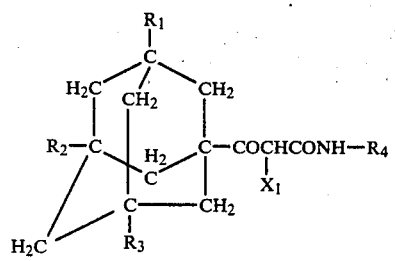

(I)

wherein $R_1$, $R_2$ and $R_3$, which may be the same or different, each represents a hydrogen atom, a methyl group, or a halogen atom (for example, a bromine atom, a chlorine atom, etc.); $R_4$ represents an aryl group which may be substituted (for example, a phenyl group, a naphthyl group, etc.); and $X_1$ represents a hydrogen atom or a group capable of coupling off (for example, a nitrogen-containing heterocyclic group, an aryloxy group, a heterocycloxy group, an alkylcarbonyloxy group, etc.).

DETAILED DESCRIPTION OF THE INVENTION $R_4$ represents an aryl group having from 6 to 30 carbon atoms which may be substituted with a halogen atom, an acylamino group, an alkoxycarbonyl group, an aryloxycarbonyl group, a carbamoyl group, a sulfamoyl group, an alkyl group, an alkoxy group, an aryl group, an aryloxy group, a hydroxy group, a sulfonamido group, etc.

$X_1$ represents a hydrogen atom or a group capable of coupling off which is represented by the following general formulae (III), (IV), (V) or (VI):

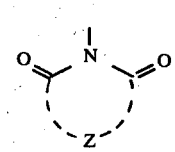

(III)

wherein Z represents the non-metallic atoms necessary to form a 4-, 5- or 6-membered ring together with

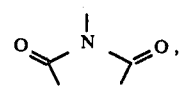

said heterocyclic ring containing optionally additional one oxygen atom, one or two nitrogen atoms or one sulfur atom as hetero atom.

(IV)

wherein R represents an aryl group having from 6 to 30 carbon atoms which may be substituted, a 5- or 6-membered heterocyclic ring containing a nitrogen atom or an oxygen atom which may be substituted, or an acyl group having from 2 to 21 carbon atoms.

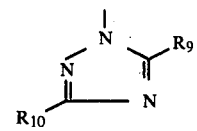

(V)

wherein $R_9$ and $R_{10}$, which may be the same or different, each represents a hydrogen atom, a halogen atom, a carboxylic acid ester group having from 2 to 21 carbon atoms, an amino group, an alkyl group having from 1 to 20 carbon atoms, an alkylthio group having from 1 to 20 carbon atoms, an alkoxy group having from 1 to 20 carbon atoms, an alkylsulfonyl group having from 1 to 20 carbon atoms, a carboxylic acid group, a sulfonic acid group, an unsubstituted or substituted phenyl group having from 6 to 20 carbon atoms, or a 5- or 6-membered heterocyclic ring containing a nitrogen atom or an oxygen atom.

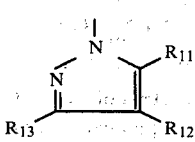
(VI)

wherein $R_{11}$, $R_{12}$ and $R_{13}$, which may be the same or different, each represents a hydrogen atom, a halogen atom, an alkyl group having from 1 to 20 carbon atoms (for example, a methyl group, an octyl group, a carboxymethyl group, etc.), an alkoxy group having from 1 to 20 carbon atoms (for example, a methoxy group, an octyloxy group, a benzyloxy group, etc.), an aryloxy group having from 6 to 20 carbon atoms (for example, a phenoxy group, a 4-methylphenoxy group, etc.), an aryl group having from 6 to 20 carbon atoms (for example, a phenyl group, a 4-methylphenyl group, etc.), an alkoxycarbonyl group having from 2 to 21 carbon atoms (for example, a methoxycarbonyl group, an octoxycarbonyl group, etc.), a carboxy group, an alkylsulfonyl group having from 1 to 20 carbon atoms (for example, a methylsulfonyl group, etc.) or a heterocyclic sulfonyl group (for example, a pyrazolylsulfonyl group, etc.).

Of the groups represented by general formula (III), the groups represented by the following general formulae (VII) to (X) are particularly preferred for $X_1$.

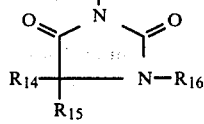
(VII)

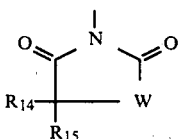
(VIII)

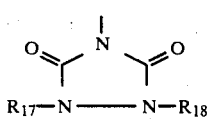
(IX)

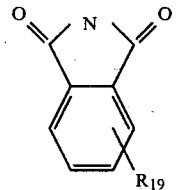
(X)

In these formulae, $R_{14}$ and $R_{15}$, which may be the same or different, each represents a hydrogen atom, an alkyl group having from 1 to 20 carbon atoms (for example, a methyl group, a dodecyl group, etc.), an aryl group having from 6 to 30 carbon atoms (for example, a phenyl group, a dodecylphenyl group, a naphthyl group, etc.), an alkoxy group having from 1- to 20 carbon atoms (for example, a methoxy group, a dodecyloxy group, etc.), an aryloxy group having from 6 to 30 carbon atoms (for example, a phenoxy group, etc.) or a hydroxy group; $R_{16}$, $R_{17}$ and $R_{18}$, which may be the same or different, each represents a hydrogen atom, an alkyl group having from 1 to 20 carbon atoms (for example, a methyl group, a dodecyl group, etc.), an aryl group having from 6 to 30 carbon atoms (for example, a phenyl group, a dodecylphenyl group, a naphthyl group, etc.), an aralkyl group having from 7 to 22 carbon atoms (for example, a substituted or unsubstituted benzyl group having 7 to 21 carbon atoms, a substituted or unsubstituted phenethyl group having from 8 to 22 carbon atoms, etc.), an acyl group having from 2 to 21 carbon atoms (for example, an acetyl group, etc.); W represents an oxygen atom or a sulfur atom; $R_{19}$ represents a monovalent substituent such as a hydrogen atom, a halogen atom, a nitro group, a cyano group, a thiocyano group, a hydroxyl group, an alkoxy group having from 1 to 20 carbon atoms (for example, a methoxy group, a dodecyloxy group, etc.), an aryloxy group having from 6 to 30 carbon atoms (for example, a phenoxy group, etc.), an acyloxy group having from 2 to 21 carbon atoms (for example, an acetyloxy group), an alkyl group having from 1 to 20 carbon atoms (for example, a methyl group, a dodecyl group, etc.), an alkenyl group having from 2 to 21 carbon atoms (for example, a vinyl group, etc.), an aryl group having from 6 to 30 carbon atoms (for example, a phenyl group, a dodecylphenyl group, a naphthyl group, etc.), an amino group, a carboxy group, an acyl group having from 2 to 21 carbon atoms (for example, an acetyl group, etc.), an alkoxycarbonyl group having from 2 to 21 carbon atoms (for example, a methoxycarbonyl group, a dodecyloxycarbonyl group, etc.), an aryloxycarbonyl group having from 7 to 31 carbon atoms (for example, a phenoxycarbonyl group, etc.), a carbamoyl group having from 1 to 20 carbon atoms (for example, a methylcarbamoyl group, etc.), an acylamino group having from 2 to 21 carbon atoms (for example, an acetylamino group, etc.), an imido group, a sulfo group, an alkylsulfonyl group having from 1 to 20 carbon atoms (for example, a methylsulfonyl group, etc.), an arylsulfonyl group having from 6 to 30 carbon atoms (for example, a phenylsulfonyl group, etc.), an alkoxysulfonyl group having from 1 to 20 carbon atoms (for example, a methoxysulfonyl group, a dodecyloxysulfonyl group, etc.), an aryloxysulfonyl group having from 6 to 30 carbon atoms (for example, a phenoxysulfonyl group, etc.), a sulfamoyl group, a sulfonamido group, a ureido group or a thioureido group.

Of the couplers represented by the general formula (I), preferred couplers are those represented by following general formula (II):

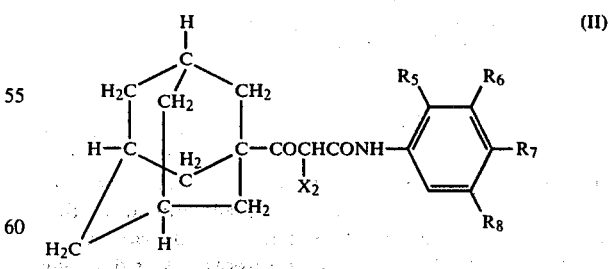
(II)

wherein $R_5$ represents a hydrogen atom, a halogen atom or an alkoxy group having from 1 to 20 carbon atoms; $R_6$, $R_7$ and $R_8$, which may be the same or different, each represents a hydrogen atom, an alkoxy group having from 1 to 20 carbon atoms, an alkoxycarbonyl group having from 2 to 21 carbon atoms, an acylamino group having from 2 to 21 carbon atoms, a sulfonylamino group having from 1 to 20 carbon atoms, a sulfamoyl group having from 1 to 20 carbon atoms or a carbamoyl group having from 1 to 20 carbon atoms.

Particularly preferred examples of the anilino group substituted with $R_5$, $R_6$, $R_7$ and $R_8$ in general formula (II) include, for example, those set forth below.

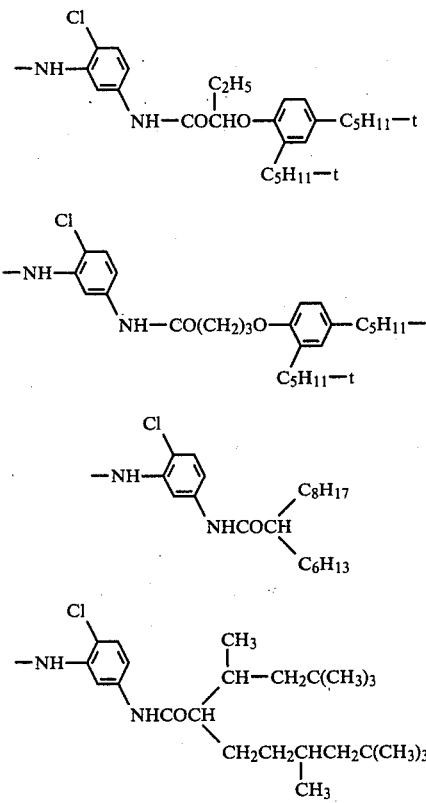

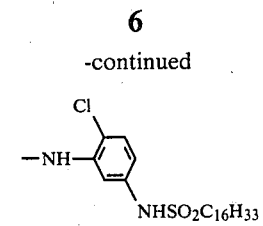

-continued

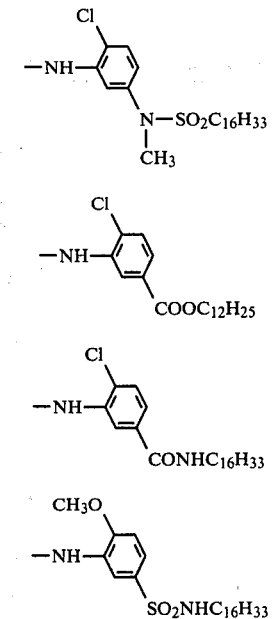

$X_2$ in general formula (II) is the same meaning as $X_1$ in general formula (I).

Specific examples of compounds according to the present invention are illustrated below but the yellow couplers which can be used in the present invention are not to be construed as being limited to these examples.

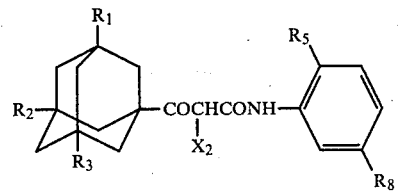

| Coupler | $R_1$ | $R_2$ | $R_3$ | $R_5$ | $R_8$ | $X_2$ |
|---|---|---|---|---|---|---|
| 1 | H | H | H | Cl | —NHCO(CH$_2$)$_3$—O—⟨C$_5$H$_{11}$-t, C$_5$H$_{11}$-t⟩ | (structure with —OC$_2$H$_5$, —N, N—CH$_2$—Ph) |
| 2 | " | " | " | " | " | (structure with CH$_3$, CH$_3$, —N, O) |

-continued
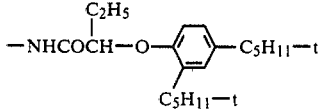
| Coupler | R1 | R2 | R3 | R5 | R8 | X2 |
|---|---|---|---|---|---|---|
| 3 | " | " | " | " | −NHCOCH(C2H5)−O−[2,4-di-($C_5H_{11}$-t)phenyl] | 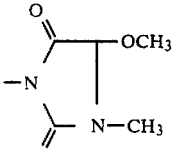 |
| 4 | " | " | " | " | " | 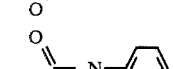 |
| 5 | " | " | " | " | −NHCOCH(C2H5)−O−[2,4-di-($C_5H_{11}$-t)phenyl] | 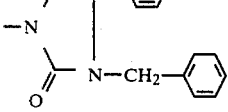 |
| 6 | " | " | " | " | " | 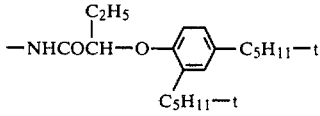 |
| 7 | " | " | " | " | " | 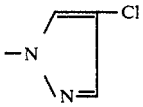 |
| 8 | " | " | " | " | " | 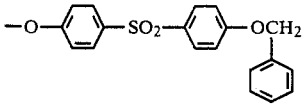 |
| 9 | Br | Br | Br | " | 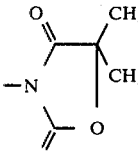 | 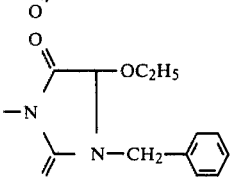 |
| 10 | $CH_3$ | H | H | −$OCH_3$ | 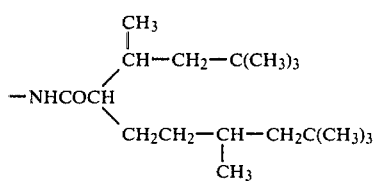 | 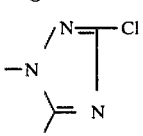 |
| 11 | H | " | " | Cl | −$NHSO_2C_{16}H_{33}$ | 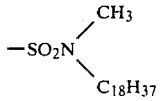 |
| 12 | " | " | " | " | −$COOC_{12}H_{25}$ | " |

-continued

| Coupler | $R_1$ | $R_2$ | $R_3$ | $R_5$ | $R_8$ | $X_2$ |
|---|---|---|---|---|---|---|
| 13 | " | " | " | " | $-COOC_3H_7$ | [imide with $-OC_{12}H_{25}$ and $N-CH_2-$phenyl] |
| 14 | " | " | " | " | $-N(CH_3)-COC_{12}H_{25}$ | [pyrazolyl] |
| 15 | [bis-adamantyl pyrazole-SO$_2$-pyrazole structure with $-COCHCONH-$(2-Cl,5-NH-COCH($C_2H_5$)-O-2,4-di-$C_5H_{11}$-t-phenyl) on each side] | | | | | |
| 16 | [bis-adamantyl diphenylsulfone-bis-ether with $-COCHCONH-$(2-Cl,5-NHCO(CH$_2$)$_3$O-2,4-di-$C_5H_{11}$-t-phenyl) on each side] | | | | | |

The yellow couplers which can be used in the present invention can be easily synthesized according to the following reaction scheme using, for example, the compound described in Japanese Patent Application (OPI) No. 73147/73 (The term "OPI" as used herein refers to a "published unexamined Japanese patent application").

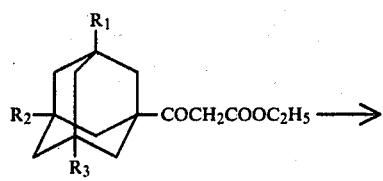

-continued

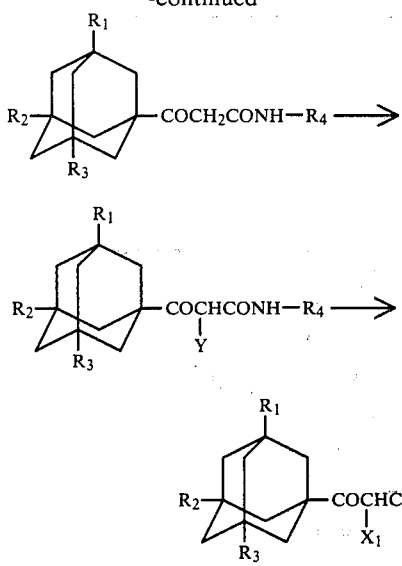

In the above formulae, $R_1$, $R_2$, $R_3$, $R_4$ and $X_1$ each has the same meaning as defined in general formula (I); and Y represents a chlorine atom or a bromine atom.

The starting materials used in the above reactions can be easily synthesized using the method described in *Chem. Ber.*, Vol. 93, p. 2055 (1960).

Specific examples of synthesizing yellow couplers used in the present invention are set forth below.

SYNTHESIS EXAMPLE 1

Synthesis of
α-(1-Adamantancarbonyl)-α-(1-benzyl-5-ethoxy-3-hydantoinyl)-2-chloro-5-[4-(2,4-di-tert-amylphenoxy)-butyramido]acetanilide [Coupler (1)]

Step (1) Synthesis of Intermediate:
α-(1-Adamantancarbonyl)-2-chloro-5-[4-(2,4-di-tert-amylphenoxy)butyramido]acetanilide A mixture of 18 g of ethyl α-(1-adamantancarbonyl)acetate and 26.7 g of 2-chloro-5-[4-(2,4-di-tert-amylphenoxy)butyramido]aniline was reacted at 140° C. under reduced pressure (1 mmHg) for 5 hours. The reaction mixture was recrystallized from a solvent mixture of hexane and ethyl acetate to obtain 19.2 g of the desired compound having a melting point of 88° to 91° C.

Step (2) Synthesis of Intermediate:
α-(1-Adamantancarbonyl)-α-chloro-2-chloro-5-[4-(2,4-di-tert-amylphenoxy)butyramido]acetanilide To a solution containing 16 g of the intermediate obtained in Step (1) and 100 ml of chloroform, 3.5 g of sulfuryl chloride was dropwise added over 10 minutes. After the completion of the addition, the mixture was further reacted for 15 minutes at room temperature and atmospheric pressure and the reaction mixture poured into ice water. The chloroform layer was separated and washed three times with water. Chloroform was distilled off to obtain 15.8 g of a viscous oil. The oil was used in the next step without further purification.

Step (3) Synthesis of Coupler (1)

A solution containing 6.7 g of the intermediate (oil) obtained in Step (2) and 20 ml of chloroform was dropwise added at room temperature over 1 hour to a solution containing 4.6 g of 1-benzyl-5-ethoxyhydantoin, 1.1 g of potassium hydroxide, 2 ml of methanol and 100 ml of dimethylformamide. After the completion of the addition, the mixture was further reacted for 5 hours. The reaction mixture was poured into water and extracted with ethyl acetate. The ethyl acetate solution was washed once with a 5% aqueous sodium hydroxide solution, twice with water, once with diluted hydrochloric acid and then twice with water. Ethyl acetate was distilled off and the residue recrystallized from a solvent mixture of hexane and ethyl acetate to obtain 6 g of the desired compound having a melting point of 141° to 142° C.

SYNTHESIS EXAMPLE 2

Synthesis of
α-(1-Adamantancarbonyl)-α-(2,4-dioxo-5,5-dimethyl-3-oxazolidinyl)-2-chloro-5-[4-(2,4-di-tertamylphenoxy)-butyramido]acetanilide [Coupler (2)]

A solution containing 6.7 g of the intermediate (oil) obtained in Step (2) of Synthesis Example 1 and 100 ml of chloroform was dropwise added at room temperature over 1 hour to a solution containing 1.9 g of 2,4-dioxo-5,5-dimethyl-3-oxazolidine, 0.82 g of potassium hydroxide, 2 ml of methanol and 100 ml of dimethylformamide. After completion of the addition, the mixture was further reacted at room temperature and atmospheric pressure for 5 hours. The reaction mixture was treated in the same manner as described in Synthesis Example 1 and the residue obtained was recrystallized from a solvent mixture of hexane and ethyl acetate to obtain 5.8 g of the desired compound having a melting point of 186.5° to 187.5° C.

In order to produce a silver halide color photographic photosensitive material in accordance with the present invention, a coupler in accordance with the present invention may be employed alone or two or more of such couplers may be employed as a mixture.

Advantageously, the coupler in accordance with the present invention can be dispersed in a photographic emulsion as a solution in an organic solvent. Specific examples of procedures and solvents used for dispersing the couplers are illustrated in detail in U.S. Pat. No. 3,676,131. The organic solvent useful for dissolving the coupler should be sparingly soluble in water and have a high boiling point, such as substituted hydrocarbons, carboxylic acid esters, benzoic acid ester, citric acid ester, carboxylic acid amides, phosphoric acid esters, ethers and the like. Representative examples thereof include di-n-butyl phthalate, di(2-ethylhexyl)phthalate, n-octyl benzoate, o-acetyltributyl citrate, tricresyl phosphate, tri-n-hexyl phosphate, and N,N-diethylcaprylamide. It is also advantageous to employ, in addition to the above-mentioned high boiling solvents, an auxiliary solvent having a low boiling point in order to facilitate the dissolution of the coupler. Representative examples thereof include propylene carbonate, ethyl acetate, butyl acetate, cyclohexanol, tetrahydrofuran and cyclohexanone.

In order to facilitate dispersion of the solvent and coupler in a hydrophilic colloid used in the photographic emulsion in a minutely dispersed form, it is advantageous to employ a surfactant.

Diffusion resistant couplers having a carboxylic acid group or a sulfonic acid group together with a ballast group in the molecule are soluble in a neutral or weakly alkaline aqueous solution (for example, about 4 wt%

NaOH or KOH aqueous solution). Such an aqueous solution containing the coupler(s) per the invention can be added to a photographic emulsion in a conventional manner.

The amount of the coupler(s) used is generally from about 5 to 1,500 g per mol of silver halide, but the amount added can vary depending on various application purposes; preferably such amount is from 10 to 500 g per mol of silver halide.

It is possible to incorporate in a color photographic light-sensitive material containing the coupler or couplers in accordance with the present invention the following couplers together with the coupler(s) according to the present invention.

Conventional open chain ketomethylene type couplers can be employed as yellow couplers. Of these couplers, benzoyl acetanilide type and pivaloyl acetanilide type compounds are especially effective. Specific examples of yellow couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Applications (OLS) Nos. 2,219,917, 2,261,361 and 2,414,006, British Pat. No. 1,425,020, Japanese Patent Publication No. 10783/76, Japanese Patent Applications Nos. (OPI) 26133/72, 73147/73, 102636/76, 6341/75, 123342/75, 130442/75, 21827/76, 87650/75, 82424/77 and 115219/77.

Pyrazolone type compounds, indazolone type compounds, cyanoacetyl compounds, etc., can be employed as magenta couplers, and particularly preferred couplers are pyrazolone type compounds. Specific examples of magenta couplers which can be employed are those described, for example, in U.S. Pat. Nos. 2,600,788, 2,983,608, 3,062,653, 3,127,269, 3,311,476, 3,419,391, 3,519,249, 3,558,319, 3,582,322, 3,615,506, 3,834,908 and 3,891,445, West German Pat. No. 1,810,464, West German Patent Applications (OLS) Nos. 2,408,665, 2,417,945, 2,418,959 and 2,424,467, Japanese Patent Publication No. 6031/65, Japanese Patent Applications (OPI) Nos. 20826/76, 58922/77, 129538/74, 74027/74, 159336/75, 42121/77, 74028/74, 60233/75, 26541/76 and 55122/78, etc.

Phenol type compounds, naphthol type compounds, etc., can be employed as cyan couplers. Specific examples of cyan couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Applications (OLS) Nos. 2,414,830 and 2,454,329, Japanese Patent Applications (OPI) Nos. 59838/73, 26034/76, 5055/73, 146828/76, 69624/77 and 90932/77, etc.

Colored couplers which can be employed include those described, for example, in U.S. Pat. Nos. 3,476,560, 2,521,908 and 3,034,892, Japanese Patent Publications 2016/69, 22335/63, 11304/67 and 32461/69, Japanese Patent Applications (OPI) Nos. 26034/76 and 42121/77, German Patent Application (OLS) Nos. 2,418,959, etc.

DIR couplers which can be employed include those described, for example, in U.S. Pat. Nos. 3,227,554, 3,617,291, 3,701,783, 3,790,384 and 3,632,345, German Patent Applications (OLS) Nos. 2,414,006, 2,454,301 and 2,454,329, British Pat. No. 953,454, Japanese Patent Applications (OPI) Nos. 69624/77, 122335/74, Japanese Patent Publication No. 16141/76, etc.

In addition to DIR couplers, other compounds which release development inhibitors upon development can also be present in the light-sensitive material. For example, such DIR compounds as are described in U.S. Pat. Nos. 3,297,445 and 3,379,529, German Patent Application (OLS) No. 2,417,914, Japanese Patent Applications (OPI) Nos. 15271/77 and 9116/78, etc., can be employed.

The coupler according to the present invention may be used in various silver halide-light-sensitive materials such as color negative films, color positive films, color reversal films, color paper and various other color light-sensitive materials, among which it is especially preferably used in color paper.

The coupler in accordance with the present invention may be used in a multilayer color light-sensitive material (such as those described in U.S. Pat. Nos. 3,726,681 and 3,516,831, British Pat. Nos. 818,687 and 923,045, etc.), in a method as described in Japanese Patent Application (OPI) No. 5179/75, in a method as described in West German Patent Application (OLS) No. 2,322,165, or used in combination with DIR compounds as described in U.S. Pat. No. 3,703,375.

In the practice of the present invention, known color fading preventing agents as described below can be employed. These color fading preventing agents can be used individually or as a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921; gallic acid derivatives as described in U.S. Pat. Nos. 3,457,079 and 3,069,262, p-alkoxyphenols as described in U.S. Pat. Nos. 2,735,765 and 3,698,909 and Japanese Patent Publications Nos. 20977/74 and 6623/77; p-oxyphenol derivatives as described in U.S. Pat. Nos. 3,432,300, 3,573,050, 3,574,627 and 3,764,337, Japanese Patent Applications (OPI) Nos. 35633/77, 147434/77 and 152225/77; bisphenol derivatives as described in U.S. Pat. No. 3,700,455, etc.

The hydrophilic colloid layers of the light-sensitive material according to the present invention can contain ultraviolet light absorbing agents. For example, benzotriazole compounds substituted with aryl groups (for example, those described in U.S. Pat. No. 3,533,794), 4-thiazolidone compounds (for example, those described in U.S. Pat. Nos. 3,314,794 and 3,352,681), benzophenone compounds (for example, those described in Japanese Patent Application (OPI) No. 2784/71), cinnamic acid ester compounds (for example, those described in U.S. Pat. Nos. 3,705,805 and 3,707,375), butadiene compounds (for example, those described in U.S. Pat. No. 4,045,229) or benzoxazole compounds (for example, those described in U.S. Pat. No. 3,700,455) can be employed. Furthermore, the compounds described in U.S. Pat. No. 3,499,762 and Japanese Patent Application (OPI) No. 48535/79 can also be used. Ultraviolet light-absorbing couplers (for example, α-naphthol type cyan color-forming couplers) and ultraviolet light-absorbing polymers can also be employed. These ultraviolet absorbing agents can also be mordanted in a specific layer(s), if desired.

The coupler according to the present invention may be employed even in a low silver amount photographic material in which the amount of a silver halide in the emulsion layer is from one half to one-hundredth the amount employed in ordinary photographic materials.

With such a color photosensitive material having a reduced content of a silver halide, an adequate color image can be obtained by a color image-forming method involving increasing the amount of a dye formed utilizing color intensification, which employs a peroxide, a cobalt complex, sodium chlorite (for example, as described in West German Patent Application (OLS) No. 2,357,694, U.S. Pat. Nos. 3,674,490, 3,761,265, West German Patent Applications (OLS) Nos. 2,044,833, 2,056,359, 2,056,360, 2,226,770, Japanese Patent Applications (OPI) Nos. 9728/73, 9729/73, etc.), or the like.

In order to color develop a photosensitive material containing a coupler in accordance with the invention, conventional methods may be followed. More Specifically, a dye image and a silver image are formed by color development with a substituted p-phenylenediamine, the silver is subsequently oxidized in a bleaching bath, and the remaining silver halide and other silver salts are removed by dissolution in a fixing bath, leaving only the dye image. Various baths such as a prehardener, a neutralizer, a first developer, an image stabilizer, etc., may also be employed in combination with the foregoing as desired or necessary.

Various known compounds may be employed as the substituted p-phenylenediamine for developing a color photosensitive material in accordance with the invention. Especially useful p-phenylenediamine type color developing agents are N,N-dialkyl-p-phenylenediamine type compounds, in which the alkyl and phenyl groups may be substituted. Among these, particularly useful compounds include, for example, N,N-diethyl-p-phenylenediamine hydrochloride, N-methyl-p-phenylenediamine hydrochloride, N,N-dimethyl-p-phenylenediamine hydrochloride, 2-amino-5-(N-ethyl-N-dodecylamino)toluene, N-ethyl-N-(β-methanesulfonamidoethyl-3-methyl-4-aminoaniline sulfate, N-ethyl-N-β-hydroxyethylaminoaniline, 4-amino-N-(2-methoxyethyl)-N-ethyl-3-methylaniline-p-toluenesulfonate, N,N-diethyl-3-methyl-4-aminoaniline, and N-ethyl-N-(β-hydroxyethyl)-3-methyl-4-aminoaniline.

Examples of useful bleaching agents include persulfates, bichromates, red prussiate (i.e., potassium ferricyanide), hydrogen peroxide, and ferric ion complex salts. Ferric ion complex salts are complexes of a ferric ion and a chelating agent, such as an amino polycarboxylic acid, an amino polyphosphonic acid, their salts, and so forth. The amino polycarboxylic acid salts or the amino polyphosphonic acid salts are salts of amino polycarboxylic acids or amino polyphosphonic acids with alkali metals, ammonia, water-soluble amines, etc. The ferric ion complex salt may be employed in the form of the complex salt, or may be produced in situ using ferric sulfate, ferric chloride, ammonium ferric nitrate, ferric phosphate or the like and a chelating agent such as an amino polycarboxylic acid or an amino polyphosphonic acid in solution.

A photosensitive material containing a coupler in accordance with the invention is characterized by reduced staining even when processed in a bleaching bath containing a strong oxidizing agent such as a bichromate or red prussiate, thus yielding a color image of excellent quality.

Examples of fixing agents that can be used include thiosulfates (e.g., ammonium thiosulfate, sodium thiosulfate, potassium thiosulfate, etc.), thiocyanates (e.g., ammonium thiocyanate, sodium thiocyanate, potassium thiocyanate, etc.), and thioether compounds (e.g., 3,6-dithia-1,8-octanediol, etc.). These fixing agents may be employed alone or as mixtures thereof.

While couplers in accordance with this invention may be used in photographic elements, in general, i.e., in conventional silver halide color photosensitive materials such as color negative films, color paper, color positive films, color reversal films for slides, color reversal films for motion pictures, color reversal films for television, etc., they are preferably used in color paper because they especially exhibit excellent color developing performance in processes using such materials.

The invention will now be more particularly illustrated by the following Examples. Unless otherwise indicated, all parts, percentages, ratios and the like are by weight.

EXAMPLE 1

27 g of the above-described Coupler (1), 13.5 ml of dioctyl-butyl phosphate as a coupler solvent, and 50 ml of ethyl acetate were heated to 70° C. to provide a solution, which solution was then added to 300 ml of an aqueous solution containing 50 g of gelatin and 2.0 g of sodium dodecylbenzenesulfonate, stirred, and heated at 50° C. for 1 hour before passage through a conventional colloid mill 5 times. As a result, the coupler together with the solvent were finely emulsified and dispersed.

The total amount of the thus-obtained emulsified dispersion was added to 1.0 kg of a photographic emulsion containing 54 g of silver iodobromide and 60 g of gelatin, and 30 ml of a 5% triethylene phosphoramide (as a hardening agent) in acetone were added and the mixture, after pH adjusting to 6.0, was coated on a cellulose triacetate film base to provide a dry thickness of 5.0 microns and dried. This was designated Sample A.

Using emulsified dispersions containing 27 g of each of the above-mentioned Coupler (2), the above-mentioned Coupler (7) and Couplers (a) and (b) which form the same dyes as those formed from the couplers according to the present invention (and which are described in U.S. Pat. No. 3,265,506) as comparative compounds in place of the above Coupler (1), following the same procedure as described above films were prepared. These films were designated Samples B, C, D and E, respectively.

Each of these films was exposed to light for sensitometry and subjected to the following process:

| Color Developing Process | Temperature (°C.) | Time |
|---|---|---|
| 1. Color development | 33 | 3 min 30 sec |
| 2. Bleach-fix | 33 | 1 min 30 sec |
| 3. Washing with water | 26 | 2 min |
| 4. Drying | | |

The process solutions used in the above color developing process had the following compositions:

| Color Development Solution | | |
|---|---|---|
| Benzyl alcohol | 15 | ml |
| Potassium carbonate | 30 | g |
| Potassium bromide | 0.5 | g |
| Hydroxylamine sulfate | 2 | g |
| Sodium sulfite | 2 | g |
| Diethylenetriamine quinqueacetate | 1 | g |
| N-Ethyl-N-β-methanesulfonamidoethyl-3-methyl-4-aminoaniline sulfate | 4.5 | g |
| Water to make | 1 | l |

-continued

| Bleach-Fix Solution | |
|---|---|
| Ammonium thiosulfate (70%) | 150 ml |
| Sodium sulfite | 5 g |
| Na[Fe(EDTA)] | 40 g |
| EDTA disodium salt | 4 g |
| Water to make | 1 l |

The thus obtained developed films were subjected to a light stability test, i.e., samples were placed in a xenon testing apparatus and exposed to $1 \times 10^6$ lux light for 16 days, whereafter the percentage in color density reduction of light exposed samples and of unexposed samples were compared.

The results of the measurement of percentages of color density reduction of the color images at initial densities of 0.50 and 1.50 are shown in Table 1 below.

Comparative compounds (a) and (b) have the following structural formulae, respectively.

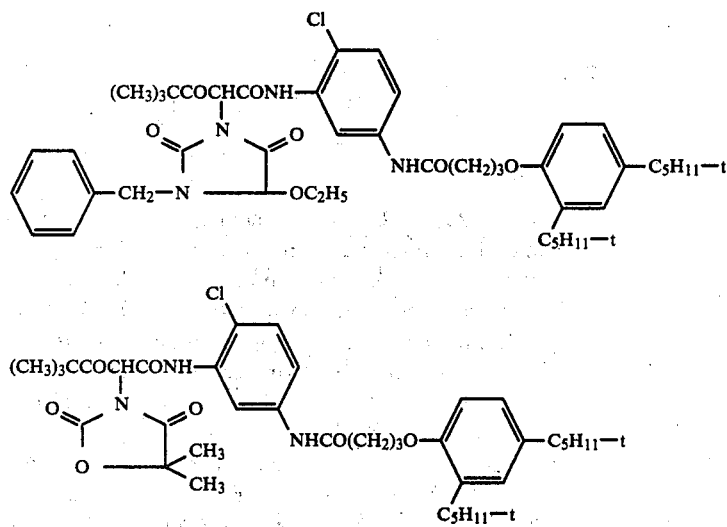

TABLE 1

| | | Percentage of Reduction in Color Density | |
|---|---|---|---|
| Sample | Coupler | Initial Density 0.5 | Initial Density 1.5 |
| A | (1) | 26 | 24 |
| B | (2) | 28 | 26 |
| C | (7) | 19 | 17 |
| D | (a) | 48 | 47 |
| E | (b) | 50 | 47 |

As is clear from the results in Table 1, Samples A, B, and C using the compounds of the present invention showed excellent lowered color image fading under light as compared with comparative samples D and E.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material containing a yellow color coupler represented by the following general formula:

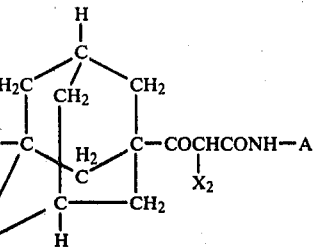

wherein $X_2$ represents a hydrogen atom or a group capable of coupling off; and A is a group selected from the group consisting of

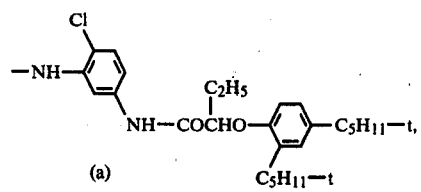

(a)

(b)

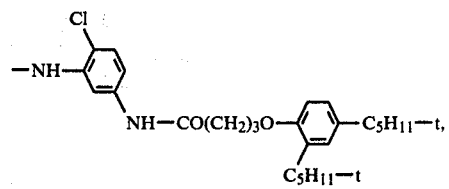

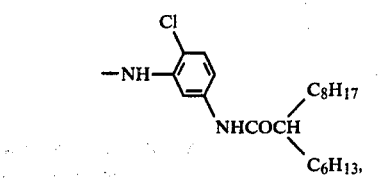

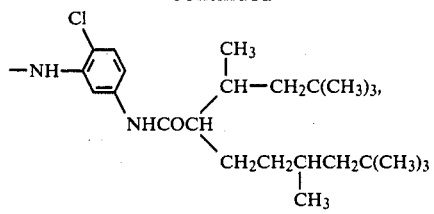

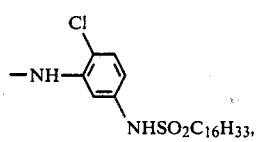

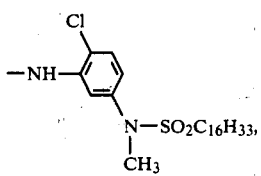

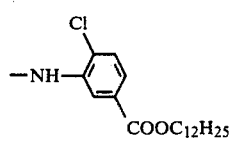

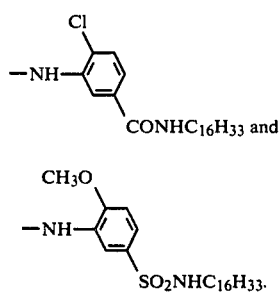

2. The silver halide color photographic light-sensitive material as claimed in claim 1, wherein $X_2$ represents a hydrogen atom.

3. The silver halide color photographic light-sensitive material as claimed in claim 1, wherein $X_2$ represents a group capable of coupling off.

4. The silver halide color photographic light-sensitive material as claimed in claim 3, wherein said group capable of coupling off is a nitrogen-containing heterocyclic group, an aryloxy group, a heterocycloxy group or an alkylcarbonyloxy group.

5. The silver halide color photographic light-sensitive material as claimed in claim 3, wherein said group capable of coupling off is a group represented by the following general formula (III), (IV), (V) or (VI):

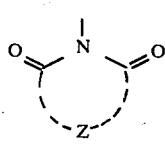

(III)

wherein Z represents the non-metallic atoms necessary to form a 4-, 5- or 6-membered ring together with

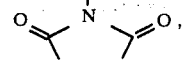

said heterocyclic ring containing optionally additionally one oxygen atom, one or two nitrogen atoms or one sulfur atom as hetero atoms;

(IV)

wherein R represents an aryl group having 6 to 30 carbon atoms which may be substituted, a 5- or 6-membered heterocyclic ring containing a nitrogen atom or an oxygen atom which may be substituted, or an acyl group having from 2 to 21 carbon atoms;

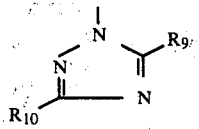

(V)

wherein $R_9$ and $R_{10}$, which may be the same or different, each represents a hydrogen atom, a halogen atom, a carboxylic acid ester group having from 2 to 21 carbon atoms, an amino group, an alkyl group having from 1 to 20 carbon atoms, an alkylthio group having from 1 to 20 carbon atoms, an alkoxy group having from 1 to 20 carbon atoms, an alkylsulfonyl group having from 1 to 20 carbon atoms, a carboxylic acid group, a sulfonic acid group, an unsubstituted or substituted phenyl group having from 6 to 20 carbon atoms, or a 5- or 6-membered heterocyclic ring containing a nitrogen atom or an oxygen atom;

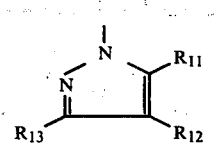

(VI)

wherein $R_{11}$, $R_{12}$ and $R_{13}$, which may be the same or different, each represents a hydrogen atom, a halogen atom, an alkyl group having from 1 to 20 carbon atoms, an alkoxy group having from 1 to 20 carbon atoms, an aryloxy group having from 6 to 20 carbon atoms, an aryl group having from 6 to 20 carbon atoms, an alkoxycarbonyl group having from 2 to 21 carbon atoms, a carboxy group, an alkylsulfonyl group having from 1 to 20 carbon atoms or a heterocyclic sulfonyl group.

6. The silver halide color photographic light-sensitive material as claimed in claim 5, wherein said group capable of coupling off represents a group represented by the following general formula (VII), (VIII), (IX) or (X):

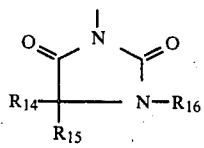 (VII)

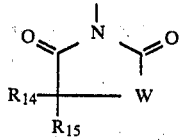 (VIII)

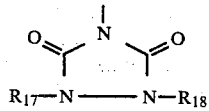 (IX)

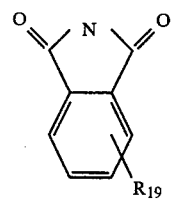 (X)

wherein $R_{14}$ and $R_{15}$, which may be the same or different, each represents a hydrogen atom, an alkyl group having from 1 to 20 carbon atoms, an aryl group having from 6 to 30 carbon atoms, an alkoxy group having from 1 to 20 carbon atoms, an aryloxy group having from 6 to 30 carbon atoms or a hydroxy group; $R_{16}$, $R_{17}$ and $R_{18}$, which may be the same or different, each represents a hydrogen atom, an alkyl group having from 1 to 20 carbon atoms, an aryl group having from 6 to 30 carbon atoms, an aralkyl group having from 7 to 22 carbon atoms, an acyl group having from 2 to 21 carbon atoms; W represents an oxygen atom or a sulfur atom; $R_{19}$ represents a monovalent substituent selected from the group consisting of a hydrogen atom, a halogen atom, a nitro group, a cyano group, a thiocyano group, a hydroxyl group, an alkoxy group having from 1 to 20 carbon atoms, an aryloxy group having from 6 to 30 carbon atoms, an acyloxy group having from 2 to 21 carbon atoms, an alkyl group having from 1 to 20 carbon atoms, an alkenyl group having from 2 to 21 carbon atoms, an aryl group having from 6 to 30 carbon atoms, an amino group, a carboxy group, an acyl group having from 2 to 21 carbon atoms, an alkoxycarbonyl group having from 2 to 21 carbon atoms, an aryloxycarbonyl group having from 7 to 31 carbon atoms, a carbamoyl group having from 1 to 20 carbon atoms, an acylamino group having from 2 to 21 carbon atoms, an imido group, a sulfo group, an alkylsulfonyl group having from 1 to 20 carbon atoms, an arylsulfonyl group having from 6 to 30 carbon atoms, an alkoxysulfonyl group having from 1 to 20 carbon atoms, an aryloxysulfonyl group having from 6 to 30 carbon atoms a sulfamoyl group, a sulfonamido group, a ureido group or a thioureido group.

7. The silver halide color photographic light-sensitive material is claimed in claim 1, wherein said coupler is present in a silver halide emulsion layer.

8. The silver halide color photographic light-sensitive material as claimed in claim 7, wherein said coupler is present in an amount of 5 to 1,500 g per mol of silver halide.

9. The silver halide color photographic light-sensitive material as claimed in claim 7, wherein said coupler is present in an amount of 10 to 500 g per mol of silver halide.

10. A silver halide color photographic light sensitive material which comprises a support having thereon a silver halide emulsion layer containing a yellow color coupler represented by the general formula

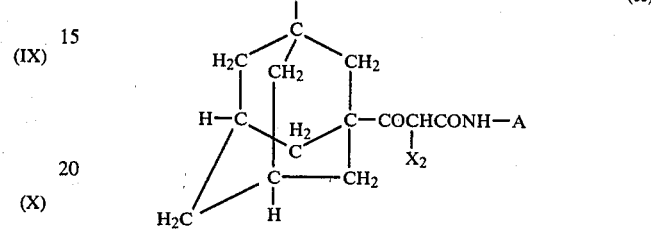 (II)

wherein $X_2$ represents a hydrogen atom or a group capable of coupling off; and A is a group selected from the group consisting of

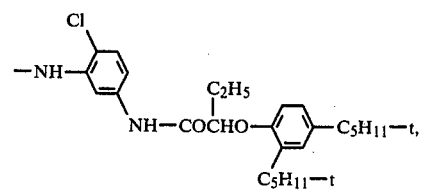

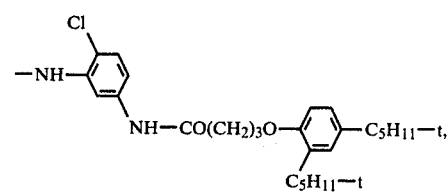

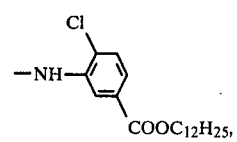

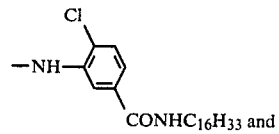

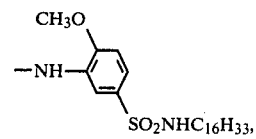

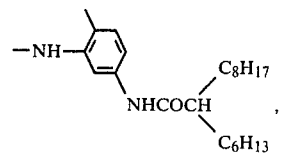

-continued

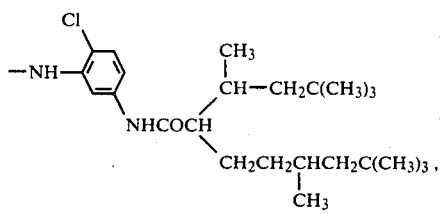

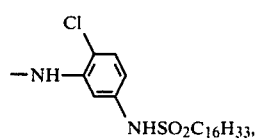

-continued

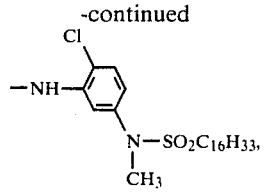

11. The silver halide color photographic light-sensitive material as claimed in claim 10, wherein said silver halide emulsion layer is a blue-sensitive silver halide emulsion layer.

12. The silver halide color photographic light-sensitive material as claimed in claim 11, wherein said color photographic material further contains a green-sensitive silver halide emulsion layer containing a magenta color coupler and a red-sensitive silver halide emulsion layer containing a cyan color coupler.

* * * * *